United States Patent [19]

Pfirmann et al.

[11] Patent Number: 5,384,413
[45] Date of Patent: Jan. 24, 1995

[54] PROCESS FOR THE PREPARATION OF TETRAFLUOROPHTHALIC ACID AND/OR TETRAFLUOROPHTHALIC ANHYDRIDE

[75] Inventors: Ralf Pfirmann, Griesheim; Theodor Papenfuhs, Frankfurt, both of Germany

[73] Assignee: Hoechst Aktiengesellschaft, Frankfurt am Main, Germany

[21] Appl. No.: 90,794

[22] Filed: Jul. 12, 1993

[30] Foreign Application Priority Data

Jul. 10, 1992 [DE] Germany .............. 4222719

[51] Int. Cl.⁶ .......................... C07D 307/83
[52] U.S. Cl. ..................... 549/246; 549/247; 549/248; 562/483; 562/494; 203/15; 203/67; 203/68; 203/69; 203/70; 203/70
[58] Field of Search ......... 549/246, 247, 248; 562/483, 494; 203/15

[56] References Cited

U.S. PATENT DOCUMENTS

| | | | |
|---|---|---|---|
| 4,769,493 | 9/1988 | Ito et al. ........................ | 562/480 |
| 5,086,188 | 2/1992 | Fertel et al. ................... | 549/246 |
| 5,179,230 | 1/1993 | Papenfuhs ...................... | 562/493 |

FOREIGN PATENT DOCUMENTS

| | | |
|---|---|---|
| 0140482 | 5/1985 | European Pat. Off. . |
| 0218111 | 4/1987 | European Pat. Off. . |
| 0259663 | 10/1988 | European Pat. Off. . |
| 0510490 | 2/1993 | European Pat. Off. . |

*Primary Examiner*—Mary C. Lee
*Assistant Examiner*—Jacqueline Haley
*Attorney, Agent, or Firm*—Connolly and Hutz

[57] ABSTRACT

The present invention relates to a process for the preparation of tetrafluorophthalic acid and/or tetrafluorophthalic anhydride by reacting a compound of the formula

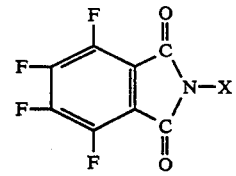

in which X is a radical

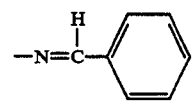

which is optionally mono- or polysubstituted on the aromatic nucleus by fluorine and/or chlorine and/or alkyl groups having 1 to 4 carbon atoms, or is a radical

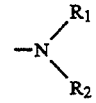

in which $R_1$, $R_2$ and $R_3$ are as defined, with water, and subsequently removing the water still present by azeotropic distillation or extracting the tetrafluorophthalic acid and/or its anhydride with a water-insoluble solvent or solvent mixture.

25 Claims, No Drawings

PROCESS FOR THE PREPARATION OF TETRAFLUOROPHTHALIC ACID AND/OR TETRAFLUOROPHTHALIC ANHYDRIDE

DESCRIPTION

The present invention relates to a process for the preparation of tetrafluorophthalic acid and/or tetrafluorophthalic anhydride.

Tetrafluorophthalic acid, like tetrafluorophthalic anhydride, which can be converted into tetrafluorophthalic acid in a simple manner, is a very important precursor for the preparation of antibacterial agents (DE-A 3 318 145, EP 0 309 789, EP 0 424 850, EP 0 424 851 and EP 0 271 275). Moreover, tetrafluorophthalic acid or tetrafluorophthalic anhydride plays an important role in the preparation of polymers (JP 02/29406), and also in the preparation of liquid crystals or photosensitive materials (JP 01/268662 and JP 11955 (1986)) which have advantageous properties.

Various routes for the preparation of tetrafluorophthalic acid are described in the literature.

For example, tetrafluorophthalic acid can be prepared from tetrachlorophthaloyl chloride (G. G. Yakobson et al., Zh. Obshsh. Khim. 36 (1966), 139; EP 0 140 482 and GB 2 146 635), from tetrachloroanthranilic acid (S. Hayashi et al., Bull. Chem. Soc. Jap. 45 (1972), 2909), from 1,2,3,4-tetrafluorobenzene (L. J. Belf et al., Tetrahedron 23 (1967), 4719 and Z. Naturforsch. 31B (1976), 1667), from tetrachlorophthalic anhydride (DE-A 3 810 093 and EP 0 218 111) or from tetrachlorophthalodinitrile (GB 2 134 900) via steps which are sometimes expensive and/or can be realized only with difficulty, if at all, industrially. The same comment also applies to the preparation of tetrafluorophthalic acid from 1,2-dibromotetrafluorobenzene (C. Tamborski et al., J. Organometallic Chem., 10 (1967), 385) and the method described by P. Sartori et al. (Chem. Ber. 101 (1968), 2004), which starts from octafluoronaphthalene. N-carbon-substituted tetrachlorophthalimides (EP 0 259 663) are likewise employed. After fluorination, these can be reacted via sometimes non-selective steps (JP 02/145 538) without intermediate isolation of the tetrafluorophthalic acid, but with isolation of one of its functional derivatives, to give 2,3,4,5-tetrafluorobenzoic acid, which is also an important precursor for synthesis of antibacterial agents. The functional derivatives intermediately isolated can be hydrolyzed to tetrafluorophthalic acid.

As the preceding statements show, there has been no lack of attempts in the past to develop processes for the preparation of tetrafluorophthalic acid. However, it can also be seen that the processes of the prior art either start from starting substances which are accessible only with great difficulty, or can be realized only at great expense, and furthermore leave something to be desired in respect of the degree of conversion and the selectivity of the reaction.

There is therefore a need for a process which on the one hand starts from starting substances which are accessible relatively easily, and on the other hand can be realized with the minimum possible technical expenditure, and moreover keep the requirement of auxiliaries and the amount of waste products obtained low.

This object is achieved by a process for the preparation of tetrafluorophthalic acid and/or tetrafluorophthalic anhydride. It comprises reacting a compound of the formula

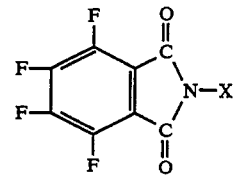

in which X is a radical

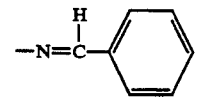

which is optionally mono- or polysubstituted on the aromatic nucleus by fluorine and/or chlorine and/or alkyl groups having 1 to 4 carbon atoms, or is a radical

in which $R_1$ and $R_2$ are identical or different and are a hydrogen atom, an alkyl group having 1 to 10 carbon atoms, an alkyl—CO— group having 1 to 6 carbon atoms in the alkyl radical or an aryl group or aryl—CO— group which is optionally mono- or polysubstituted on the aromatic nucleus by fluorine and/or chlorine and/or alkyl groups having 1 to 4 carbon atoms, or $R_1$ and $R_2$ together form a radical of the formula

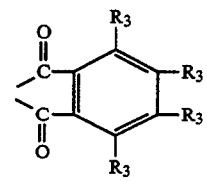

in which $R_3$ is a hydrogen atom, a chlorine atom or a fluorine atom, with water, and subsequently removing the water still present by azeotropic distillation or extracting the tetrafluorophthalic acid and/or its anhydride with a water-insoluble solvent or solvent mixture.

The compounds of the abovementioned formula are N′-substituted N-aminotetrafluorophthalimides, which can be prepared, for example, in a comparatively simple manner starting from tetrachlorophthalic anhydride by reaction with hydrazine sulfate in sulfuric acid and subsequent chlorine/fluorine exchange.

Suitable N′-substituted N-aminotetrafluorophthalimides are N′-dialkylaminotetrafluorophthalimides, N′-diacylaminotetrafluorophthalimides, 2,3,4,5-tetrafluorobisphthalimides, octafluorobisphthalimide, N′-acylalkylaminotetrafluorophthalimides and substituted N′-benzylideneaminotetrafluorophthalimides, in particular N′-dimethylaminotetrafluorophthalimide, 2,3,4,5-tetrafluorobisphthalimide, octafluorobisphthalimide, N′-methylbenzoyltetrafluorophthalimide and N′-benzylideneaminotetrafluorobisphthalimide, and preferably N'-benzylideneaminotetrafluorobisphthalimide, N'-diacetylaminotetrafluorobisphthalimide and octafluorobisphthalimide.

The process according to the invention can be carried out particularly advantageously using octafluorobisphthalimide. Hydrolysis of one mole of octafluorobisphthalimide results in 2 mol of tetrafluorophthalic acid, which can be converted into tetrafluorophthalic anhydride if appropriate. This makes the reaction particularly simple, and also leads to further by-products originating from the hydrolysis being avoided.

The reaction can be carried out without great expense using water, and addition of auxiliaries which catalyze the reaction can be dispensed with. 10 to 10000, in particular 100 to 1000, preferably 100 to 600% by weight of water, based on the compound used as the starting substance, i.e. based on the N'-substituted N-aminotetrafluorophthalimide, if appropriate with an inert solvent, is usually employed. If an inert solvent is used, it is advisable to use 100 to 1000% by weight of water, based on the starting substance.

It is advisable to use water at least in the stoichiometrically required amount, or advantageously in a stoichiometric excess.

Another advantage of the process according to the invention is that the use of the usual acid catalysts, in particular mineral acids, can be dispensed with. This is surprising, since phthalimides in general are stable and usually can be hydrolyzed only in the presence of mineral acids (cf. also above, Houben-Weyl-Müller: Methoden der Organischen Chemie (Methods of Organic Chemistry), Volume VII (1952), 432–433; ibid. Volume E V (1985), 257–263; and T. Kojimoto, J. Tsuji, J. Org. Chem. 48 (1983), 1685).

One reason for this unusual surprising behavior could possibly be that the reaction proceeds autocatalytically. It would be conceivable that even traces of tetrafluorophthalic acid are sufficient to catalyze further hydrolysis of the phthalimides even at unusually low temperatures.

It is possible to add tetrafluorophthalic acid at the start of the hydrolysis to assist the reaction. If the intention is to assist the reaction by means of tetrafluorophthalic acid, 0.1 to 2.5% by weight of tetrafluorophthalic acid is used, based on the compound used as the starting substance. However, this addition is not absolutely necessary. In this connection, the use of tetrafluorophthalic acid can also be dispensed with.

Nevertheless, it is also possible to employ mineral acids as a hydrolysis catalyst. However, the corrosion caused by the hydrogen fluoride formed by side reactions in the course of the reaction is thereby additionally intensified.

Another characteristic of the reaction according to the invention is that the hydrolysis already starts to progress at relatively low temperatures. The reaction is usually carried out at 20 to 140, in particular 40 to 110, preferably 60° to 100° C. The reaction can also be carried out at lower temperatures, but at the price of correspondingly long reaction times, because the rate of reaction may be reduced. On the other hand, the reaction can also be carried out at higher temperatures, although an increased amount of cleavage products and corrosion products, where appropriate, must be expected.

The compound of the abovementioned formula used as the starting substance is employed in the reaction together with water and, if appropriate, organic solvents. The resulting aqueous mixture usually has a pH of 2 to 8, in particular 4 to 7, preferably 6 to 6.9, at the start of the reaction. The pH may change in the course of the reaction and lead to lower values, in general caused by the formation of tetrafluorophthalic acid and, where appropriate, splitting of hydrogen fluoride.

It may also be appropriate to carry out the reaction in the presence of small amounts of polar aprotic solvents, such as are contained, for example, in the N'-substituted N-aminotetrafluorophthalimide crude products obtained from the chlorine/fluorine exchange reaction. These additions lead to higher rates of reaction, possibly because of their property as solubilizing agents.

Possible polar aprotic solvents are sulfolane (tetramethylene sulfone), tetramethylene sulfoxide, N,N-diethylacetamide, N,N-dimethylacetamide, N,N-dimethylformamide, N-methylpyrrolidone, dimethyl sulfoxide, dimethyl sulfone, diphenyl sulfoxide, diphenyl sulfone, tetramethylurea, tetra-n-butylurea and 1,3-dimethylimidazolidin-2-one or mixtures thereof. The reaction mixture according to the invention contains these solvents, if appropriate, in amounts of between about 0.5% and about 10%, preferably between about 1% and about 2%.

The reaction has in general ended after about 4 to about 24 hours, depending on the size of the batch and the reaction conditions chosen. Reaction times of between about 8 and about 12 hours are often adequate, and after this period the insoluble residue is filtered off. It may be necessary to add clarifying auxiliaries, such as active charcoal or silicates, which are employed in amounts of up to about 10% by weight of the starting material employed, and/or fluoride-trapping agents, such as calcium salts, silicon dioxide and/or a substance containing silicon dioxide, for example silicic acid. Calcium salts which are to be used are, for example, calcium chloride, calcium sulfate and calcium carbonate. Silicon dioxide may be used as the fluoride-trapping agent (silicon dioxide is available commercially for example as AEROSIL TM), compounds which contain silicon dioxide, such as silicic acid or quartz. These additives are used in amounts of up to about 1 mol %, based on the compound of the abovementioned formula employed as the starting substance.

For working up the reaction mixture, the hydrazine salt formed is converted into elemental nitrogen if appropriate—if octafluorobisphthalimide is used—initially at pH 2 to 3 and in general at temperatures below about 50° C. This is effected by addition of an oxidizing agent, such as chlorine bleaching liquor, sodium nitrite or potassium nitrite or hydrogen peroxide. To accelerate the reaction, it may be appropriate to carry out the decomposition of the hydrazine salt by slowly metering in the oxidizing agent during the hydrolysis. However, it is also possible to add the oxidizing agent after the hydrolysis has been concluded.

Thereafter, either the water is distilled off azeotropically, or the aqueous solution is extracted with organic solvents.

For removal of the water by distillation, a solvent which is suitable for azeotropic distillation of water is used, such as toluene, xylene, chlorotoluene, dichlorobenzene, chloroform, methylene chloride or aliphatic hydrocarbons having 5 to 10 carbon atoms, for example hexane or cyclohexane, and the water still present is removed by means of azeotropic distillation. It is usually not tetrafluorophthalic acid but tetrafluorophthalic anhydride which is obtained here, depending on the process parameters chosen.

The organic solvents used for extraction of the tetrafluorophthalic acid can be dialkyl ethers having 1 to 10 carbon atoms in the alkyl radical, alkyl acetates having 1 to 10 carbon atoms in the alkyl radical, 3-methoxybutyl acetate or other solvents of suitable polarity. It may be particularly advantageous to carry out this extraction with trialkylamines having 4 to 20 carbon atoms per alkyl radical, preferably trialkylamines having 6 to 14 carbon atoms per alkyl radical, or mixtures thereof, if appropriate in the presence of an inert organic solvent, these amines being insoluble in the aqueous mother liquor. As is known from the literature (DE 3 627 653), these amines are suitable for extraction without trace of acid compounds, such as phenols, from dilute aqueous solutions. The amines are employed according to the invention in amounts of between about 100 mol % and about 1000 mol %, preferably between 150 mol % and about 300 mol %, based on the amount of tetrafluorophthalic acid to be extracted. The use of HOSTAREX ™ brands from Hoechst AG, in particular the brands A 324 and A 327, which are mixtures of such amines, is preferred. Analogous use of other amines, in particular heterocyclic bases, such as lutidines, collidines or quinolines, may be advantageous.

The amount of tetrafluorophthalic acid to be extracted in practice is appropriately estimated by the amount of the compound of the above formula (N'-substituted N-aminotetrafluorophthalimides) employed. For better handling of this isolation variant, the amines are in general diluted with an inert organic solvent, such as toluene, xylene, chlorinated aliphatic and aromatic hydrocarbons, for example methylene chloride, chloroform, 1,2-dichloroethane, chlorobenzene and chlorotoluene and dichlorobenzene or similar compounds, but it is also possible to carry out the reaction without a diluent. The inert solvents are usually used in amounts of between 20 and 1000, in particular between 100 and 300% by weight, based on the amine employed.

This process has the advantage that after separation of the phases, the organic phase can be heated to temperatures of between about 80° C. and about 180° C., preferably between about 120° C. and about 150° C., 2,3,4,5-tetrafluorobenzoic acid being formed with decarboxylation. The same effect can also be achieved by extracting the tetrafluorophthalic acid—as described above—and isolating it as a crude product, and then decarboxylating it in tertiary amines (JP 01/25 737 and JP 63/295 529). This variant has the advantage that the amine mixtures which are preferred according to the invention are inexpensive and can easily be recycled.

During working up of the reaction product, or in order to avoid process technologyproblems, it may be necessary to acidify the reaction mixture by addition of organic or inorganic acids, such as trifluoromethanesulfonic acid, trifluoroacetic acid, hexafluoropropanesulfonic acid, phosphoric acid, nitric acid, sulfuric acid or hydrochloric acid, small amounts of these acids already being sufficient, since pH values between 1 and 1.5 are adequate for these purposes. The melt which remains after removal of all the solvents is fractionated in vacuo, during which any auxiliaries used, such as benzaldehydes, can be partly recovered. Tetrafluorophthalic acid can be obtained very easily from the tetrafluorophthalic anhydride passing over by extraction by stirring from water or dilute mineral acid, as is known from EP 253 663 B1, Example 3. Conversely, tetrafluorophthalic acid already loses water at temperatures of about 90° C. and is thereby converted into its anhydride, as is the case with other halophthalic acids, for example with tetrachlorophthalic acid and the anhydride thereof (T. G. Delbridge, American Chemical Journal 41 (1909), 393).

The individual process steps can be carried out under atmospheric pressure, reduced pressure or increased pressure as required, the procedure under atmospheric pressure usually being preferred.

The following examples illustrate the process, without limiting it.

EXAMPLE 1

106.3 g (purity about 82%) of crude octafluorobisphthalimide are suspended in 300 g of water, and 3 g of active charcoal and 3 g of calcium chloride are added to the solution. The suspension is stirred at 95° C. for 16 hours. After cooling, the solid contained in the suspension obtained is removed by filtration, and chlorine bleach liquor is added to the filtrate until excess chlorine can be detected in the solution. The resulting mother liquor is brought to pH 1 by addition of hydrochloric acid. Extraction of the aqueous phase with methyl tert-butyl ether (MTBE), drying of the organic phase over MgSO$_4$, filtration and removal of the solvent gives 80.4 g (338 mmol, 85% of theory) of tetrafluorophthalic acid, and crystallization from 20% strength hydrochloric acid gives 75.0 g (315 mmol, 79% of theory) of tetrafluorophthalic acid (melting point 155°–157° C.).

EXAMPLE 2

500 g (pure content 340 g, about 50 g of N,N-dimethylacetamide) of crude octafluorobisphthalimide (from the chlorine/fluorine exchange reaction) are suspended in 2000 g of water, and 30 g of active charcoal and 50 g of silicic acid are added to the solution. The suspension is stirred at 100° C. for 8 hours. After cooling, the solid contained in the suspension obtained is removed by filtration and the filtrate is brought to pH 1 by addition of trifluoroacetic acid. Extraction of the aqueous phase with di-n-butyl ether, drying of the organic phase over MgSO$_4$, filtration and removal of the solvent gives 321.9 g (1.35 mol, 85% of theory) of tetrafluorophthalic acid, and crystallization from 20% strength hydrochloric acid gives 300 g (1.26 mol, 79% of theory) of tetrafluorophthalic acid (melting point 155°–157° C.).

EXAMPLE 3

100 g (pure content 71 g, about 10 g of N-methylpyrrolidone) of crude N'-dimethylamino-N-aminotetrafluorophthalimide (X=dimethylamino) are suspended in 600 g of water, and 8 g of active charcoal and 5 g of calcium sulfate are added to the solution. The suspension is stirred at 85° C. for 20 hours. After cooling, the solid contained in the suspension obtained is removed by filtration and the filtrate is brought to pH 1.5 by addition of phosphoric acid. Extraction of the aqueous phase with BUTOXLY ™ (3-methoxybutyl acetate), drying over MgSO$_4$, filtration and removal of the solvent gives 110.8 g (466 mmol, 86% of theory) of tetrafluorophthalic acid, and crystallization from 20% strength hydrochloric acid gives 95.9 g (403 mmol, 75% of theory) of tetrafluorophthalic acid (melting point 154°–157° C.).

EXAMPLE 4

50 g (pure content 33 g, about 8 g of sulfolane) of crude N'-benzylideneaminotetrafluorophthalimide (X=benzylideneamino) are suspended in 600 g of water, and 4 g of perlite and 2 g of AEROSIL ™ (Silicon dioxide) are added to the solution. The suspension is stirred at 100° C. for 16 hours. After cooling, the solid contained in the suspension is removed and the filtrate is brought to pH 1 by addition of sulfuric acid. Extraction of the aqueous phase with ethyl acetate, drying over $MgSO_4$, filtration and removal of the solvent and the benzaldehyde contained in the filtrate gives 35 g (148 mmol, 72% of theory) of tetrafluorophthalic acid (purity determined by means of high performance liquid chromatography (HPLC)).

EXAMPLE 5

100 g of crude octafluorobisphthalimide (purity determined by means of gas chromatography (GC): 75%, about 8 g residual content of N,N-dimethylacetamide) are suspended in 500 g of xylene with 10 g of water, and the solution formed on heating is stirred at 100° C. for 72 hours. The mixture is filtered hot and the filtrate is kept at 0° C. for 5 hours, while stirring. The yellow-colored tetrafluorophthalic anhydride which has precipitated is isolated by filtration. Drying gives 59.8 g (270 mmol, 79% (crude)) of tetrafluorophthalic anhydride, the mother liquor still containing small amounts of product (1 to 3%) and being used again for further batches.

EXAMPLE 6

109.0 g (250 mmol) of octafluorobisphthalimide (crystallized from ethyl acetate, melting point 302.8° C., determined by means of differential scanning calorimetry (DSC)) are suspended in 400 g of water, and 2 g of active charcoal and 5 g of calcium chloride are added to the solution. The suspension is stirred at 90° C. for 18 hours. After cooling, the solid contained in the suspension obtained is removed by filtration. Extraction of the aqueous phase by means of diisopropyl ether, drying over $MgSO_4$, filtration and removal of the solvent gives 108.3 g (460 mmol, 91%) of tetrafluorophthalic acid (total yield, crude, 86%).

EXAMPLE 7

200 g of crude octafluorobisphthalimide (purity 86%, 172 g, 394 mmol) are suspended in 1200 g of water, and 50 g of active charcoal and 50 g of silicic acid are added. The suspension is stirred at 95° C. for 10 hours. 2 hours after the start of the reaction, a solution of 63.3 g (920 mmol) of sodium nitrite in 200 g of water is added dropwise in the course of 5 hours. After cooling, a brown-colored suspension is obtained, and is brought to pH 1 by means of sulfuric acid. The solid constituents are removed by filtration and the filter cake is washed twice with 100 ml of water each time. 400 g of xylene are added to the aqueous phase, and 200 g of HOSTAREX ™ A 324 are then allowed to run in, while stirring. The mixture is stirred vigorously for 0.5 hour, the organic phase, which contains the tetrafluorophthalic acid, is separated off and the aqueous phase is discarded. The organic phase is heated at the boiling point for 4 hours, vigorous evolution of gas occurring. The brown solution is extracted by stirring twice with dilute potassium hydroxide solution, and the organic phase can be reused for the extraction. The alkaline solution is brought to pH 1 with sulfuric acid (96% strength) and extracted with MTBE. Drying and removal of the solvent gives 107.4 g (553 mmol, 70% of theory) of 2,3,4,5-tetrafluorobenzoic acid.

EXAMPLE 8

5 g of granular active charcoal, 10 g of perlite and 15 g of quartz are added to 150 g of crude octafluorobisphthalimide (purity 60%) in 250 g of water. This mixture is stirred at 100° C. for 8 hours and, after cooling, is brought to pH 2 by means of 36% strength hydrochloric acid. Chlorine bleaching liquor (13%) is then metered in underneath the surface of the liquid (evolution of gas), while stirring, until a starch iodide sample indicates an excess of oxidizing agent. The solids are filtered off at 30° C. and the filter cake is washed twice with 50 g of water. The mother liquor is brought to pH 1.5 and extracted with 200 g of 1,2-dichlorobenzene/150 g of HOSTAREX ™ A 327. Further processing is carried out as described in Example 7. In this manner, after redissolving in water, 52.1 g (268 mmol, 65% of theory) of 2,3,4,5-tetrafluorobenzoic acid (melting point 85.6°-87.5° C.) are obtained as a colorless solid.

EXAMPLE 9

350 g of crude tetrafluorophthalic acid are heated with 800 g of xylene using a water separator, until no further water passes over (5 hours). The resulting suspension is allowed to cool and the anhydride which has precipitated is filtered off. 301 g of tetrafluorophthalic anhydride are obtained, the mother liquor, which still contains about 5 g of tetrafluorophthalic anhydride, being used for further dehydrations. The tetrafluorophthalic anhydride is then purified by fractionation, whereupon it passes over as a colorless liquid (under 1 mbar/95° C.–105° C.) and solidifies as a colorless, crystalline mass of melting point 93°-94° C. 255 g (1.16 mol) of tetrafluorophthalic anhydride with a purity of >99% (GC, HPLC) are obtained in this manner.

We claim:

1. A process for the preparation of tetrafluorophthalic acid and/or tetrafluorophthalic anhydride, which comprises reacting a compound of the formula

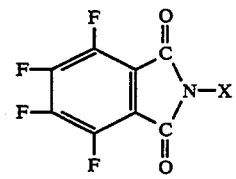

in which X is a radical

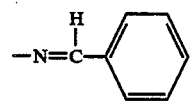

which is optionally mono- or polysubstituted on the aromatic nucleus by fluorine and/or chlorine and/or alkyl groups having 1 to 4 carbon atoms, or is a radical

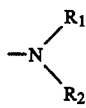

in which $R_1$ and $R_2$ are identical or different and are a hydrogen atom, an alkyl group having 1 to 10 carbon atoms, an alkyl—CO— group having 1 to 6 carbon atoms in the alkyl radical or an aryl group or aryl—CO— group which is optionally mono- or polysubstituted on the aromatic nucleus by fluorine and/or chlorine and/or alkyl groups having 1 to 4 carbon atoms, or $R_1$ and $R_2$ together form a radical of the formula

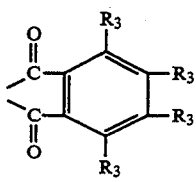

in which $R_3$ is a hydrogen atom, a chlorine atom or a fluorine atom, with water, and subsequently removing the water still present by azeotropic distillation or extracting the tetrafluorophthalic acid and/or its anhydride with a water-insoluble solvent or solvent mixture.

2. The process as claimed in claim 1, wherein octafluorobisphthalimide of the formula

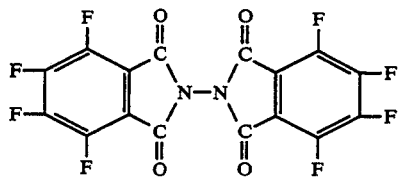

is employed as the compound.

3. The process as claimed in claim 1, wherein the reaction is carried out without addition of mineral acids.

4. The process as claimed in claim 1, wherein tetrafluorophthalic acid is added at the start of the reaction.

5. The process as claimed in claim 1, wherein 0.1 to 2.5% by weight of tetrafluorophthalic acid, based on the compound used as the starting substance is added.

6. The process as claimed in claim 1, wherein active charcoal or silicates are employed as a filtration auxiliary.

7. The process as claimed in claim 1, wherein the tetrafluorophthalic acid and/or its anhydride is extracted by means of a dialkyl ether having 1 to 10 carbon atoms per alkyl radical, an alkyl acetate having 1 to 10 carbon atoms in the alkyl radical, 3-methoxybutyl acetate, a trialkylamine having 4 to 20 carbon atoms per alkyl radical or a mixture of these amines, if appropriate in the presence of an inert organic solvent, selected from the group consisting of toluene, a xylene and a chlorinated aliphatic or aromatic hydrocarbon, selected from the group consisting of methylene chloride, chloroform, 1,2-dichloroethane, chlorobenzene, chlorotoluene and dichlorobenzene.

8. The process as claimed in claim 1, wherein a solvent suitable for azeotropic distillation of water, selected from the group consisting of toluene, xylene, chlorotoluene, dichlorobenzene, chloroform, methylene chloride, 1,2-dichloroethane and an aliphatic hydrocarbon having 5 to 10 carbon atoms, selected from the group consisting of hexane and cyclohexane, is added and the water still present is removed by means of azeotropic distillation.

9. The process as claimed in claim 1, wherein an oxidizing agent is added during the reaction or after the reaction has ended.

10. The process as claimed in claim 1, wherein, after azeotropic removal of the water still present, the mixture is filtered in the hot state and cooled, and tetrafluorophthalic anhydride is filtered off from the cooled mixture.

11. The process as claimed in claim 1, wherein the tetrafluorophthalic acid extracted in crude form is decarboxylated in a water insoluble solvent or solvent mixture to give 2, 3, 4, 5-tetrafluorobenzoic acid.

12. The process as claimed in claim 1, wherein 10 to 10000% by weight of water, based on the compound used as the starting substance is employed.

13. The process as claimed in claim 1, wherein 100 to 1000% by weight of water, based on the compound used as the starting substance is employed.

14. The process as claimed in claim 1, wherein 100 to 600% by weight of water based on the compound used as the starting substance is employed.

15. The process as claimed in claim 1, wherein an inert solvent is employed.

16. The process as claimed in claim 1, wherein the reaction is carried out at 20° to 140° C.

17. The process as claimed in claim 1, wherein the reaction is carried out at 40° to 110° C.

18. The process as claimed in claim 1, wherein the reaction is carried out at 60° to 100° C.

19. The process as claimed in claim 1, wherein the mixture has a pH of 2 to 8 at the start of the reaction.

20. The process as claimed in claim 1, wherein the mixture has a pH of 4 to 7, at the start of the reaction.

21. The process as claimed in claim 1, wherein the mixture has a pH of 6 to 6.9 at the start of the reaction.

22. The process as claimed in claim 1, wherein the reaction is carried out in the presence of a compound selected from the group consisting of calcium salts, silicon dioxide, or a substance containing silicon dioxide.

23. The process as claimed in claim 1, wherein the reaction is carried out in the presence of silicic acid.

24. The process as claimed in claim 1, wherein any hydrazine salts formed are oxidized to nitrogen by an oxidizing agent.

25. The process as claimed in claim 24, wherein the oxidizing agent is selected from the group consisting of chlorine bleaching liquor, potassium nitrite, sodium nitrite, or hydrogen peroxide.

* * * * *